United States Patent [19]

Roth

[11] 4,132,715

[45] Jan. 2, 1979

[54] PROCESS FOR THE PRODUCTION OF MALEIMIDES

[75] Inventor: Martin Roth, Basel, Switzerland

[73] Assignee: Ciba-Geigy Corporation, Ardsley, N.Y.

[21] Appl. No.: 782,682

[22] Filed: Mar. 30, 1977

[30] Foreign Application Priority Data

Apr. 9, 1976 [CH] Switzerland ........................ 4534/76

[51] Int. Cl.$^2$ ............................................ C07D 207/44

[52] U.S. Cl. ........................ 260/326.26; 260/326.5 S; 260/326.5 SF; 260/326.5 C; 260/326.5 FM; 260/326.33; 260/326.41

[58] Field of Search ................ 260/326.5 FM, 326.26, 260/326.5 S, 326.5 SF, 326.5 C

[56] References Cited

U.S. PATENT DOCUMENTS

| | | | |
|---|---|---|---|
| 2,980,694 | 4/1961 | Sauers et al. ...................... | 260/326.5 |
| 3,855,239 | 12/1974 | Crivello ......................... | 260/326.26 |

*Primary Examiner*—Jose Tovar
*Attorney, Agent, or Firm*—Luther A. R. Hall

[57] ABSTRACT

There is described a process for the production of maleimides, particularly N-substituted maleimides or N,N'-bis-maleimides, by isomerization of the corresponding isoimides in the presence of specific catalysts, such as mixtures of phenol and triethylamine. Maleimides of high purity and in good to very good yields under mild conditions and with the use of small amounts of catalyst are obtained by the process according to the invention.

11 Claims, No Drawings

PROCESS FOR THE PRODUCTION OF MALEIMIDES

The present invention relates to a process for the production of maleimides, particularly N-substituted maleimides and N,N'-bis-maleimides, from the corresponding isoimides.

A process for the conversion of N-substituted isomaleimides and N,N'-bis-isomaleimides to the corresponding maleimides and bis-maleimides, respectively, is described in U.S. Pat. No. 2,980,694. The isomerisation is performed in the presence of an anion of a lower fatty acid and optionally of a tertiary amine, preferably in the presence of sodium acetate or triethylammonium acetate. This process is disadvantageous since it requires relatively high reaction temperatures, preferably above 60° C., and large amounts of catalyst, generally between 25 and 200 mol %, relative to the starting isoimide.

N-substituted maleimides and N,N'-bis-maleimides can be produced also by reaction of corresponding maleamic acids in an organic diluent in the presence of dehydrating agents, such as acetic anhydride or acetyl chloride, of a tertiary amine or sodium acetate and, optionally, of a nickel catalyst [see German Offenlegungsschrift 2,040,094 and U.S. Pat. Nos. 2,444,536, 3,018,290 and 3,018,292]. It is necessary in these processes to use at least equimolar amounts of dehydrating agent and high amounts of sodium acetate or tertiary amine. There occur therefore considerable amounts of by-products, the reprocessing of which, if at all possible, is very difficult and expensive. Furthermore, the disposal of by-products, which cannot be re-utilised, in a manner satisfying present-day regulations governing protection of the environment is frequently problematic and very expensive, e.g. the removal of the salts occurring in the reaction in the presence of acetyl chloride or acetic anhydride and a tertiary amine.

The object of the present invention was the development of a simplified, more economical process for producing imides by conversion of corresponding isoimides under mild reaction conditions and with the avoidance of any large amounts of by-products difficult to dispose of.

It has now been found that it is possible to produce, with a high degree of purity and in good to very good yields under mild reaction conditions and with the use of small amounts of catalyst, imides of the formula I

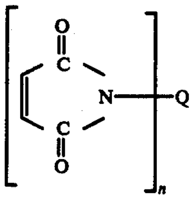

(I)

wherein n represents the number 1 or 2,

Q represents, if n is 1, an unsubstituted or substituted aryl group, and, if n is 2, an unsubstituted or substituted arylene group, or a group of the formulae

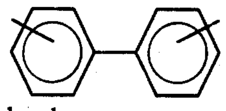 or 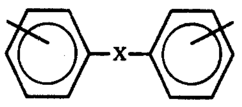 , whereby

X represents the bridge member —O—, —S—, —S—S—, —$SO_2$—, —$CH_2$—, —CO— or

—CO— or 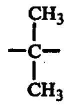 , by converting an isoimide of the formula II

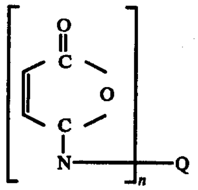

(II), wherein Q and n have the meanings given under the formula I, in the presence of a compound of the formula III $M\!-\!OH)_z$ (III)

and of a tertiary amine of the formula IV or V

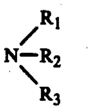 or 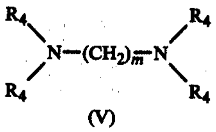

(IV) (V)

wherein z represents the number 1 or 2, m represents an integer from 2-6,

M represents, where z is 1, an unsubstituted or substituted phenyl or naphthyl group, a group

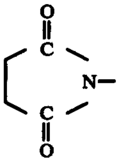 or 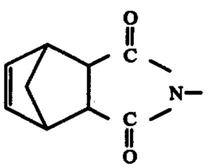 and, where z is 2, a group

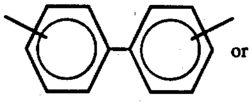 or 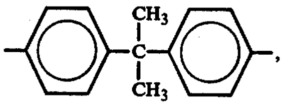, $R_1$ and $R_2$ independently of one another represent an alkyl group having 1-16 carbon atoms, a cycloalkyl group having 3-12, especially 5 or 6, carbon atoms, or benzyl, $R_3$ represents an alkyl group having 1-16 carbon atoms, phenyl, benzyl or phenylethyl, and $R_4$ represents methyl or ethyl, at a temperature of about 0–80° C., to an imide of the formula I.

Aryl or arylene groups represented by Q are, in particular, phenyl, 1- or 2-naphthyl, phenylene or naphthylene groups, especially the 1,3- or 1,4-phenylene group and the 1,2-, 1,8- or 2,3-naphthylene group. Such groups can be unsubstituted or substituted. Suitable substituents on aryl or arylene groups Q are, e.g., the following: halogen atoms, e.g. F, Cl, Br and I; hydroxyl groups; alkyl groups, particularly those having 1–8 carbon atoms; halogenoalkyl groups having 1–3 carbon atoms, such as the trifluoromethyl group; alkylthio and N,N-dialkylamino groups each preferably having 1–4 carbon atoms in the alkyl moieties; alkoxy groups, especially those having 1–4 carbon atoms; phenoxy groups; alkoxycarbonyl groups preferably having 2–5 carbon atoms, such as the methoxy-, ethoxy- and n-butoxycarbonyl group; $—SO_2Y—$, —NH—CO—Y—,

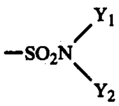

or

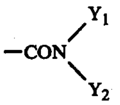

groups, wherein Y represents a phenyl group or an alkyl group preferably having 1–4 carbon atoms, $Y_1$ represents hydrogen, a phenyl or naphthyl group, or an alkyl group having 1–8, particularly 1–4, carbon atoms, and $Y_2$ represents hydrogen or an alkyl group having 1–8, especially 1–4, carbon atoms; or cyano and nitro groups. Aryl and arylene groups Q can contain 1 to 3, preferably 1 or 2, such substituents.

Q preferably represents, if n is 1, the 1- or 2-naphthyl group, or a phenyl group which is substituted by one or two halogen atoms, particularly chlorine atoms, an alkyl or alkoxy group each having 1–4, especially 1 or 2, carbon atoms in the alkyl moiety, a trifluoromethyl, sulphamoyl, nitro or cyano group. Q represents particularly preferably, if n is 1, an unsubstituted phenyl group.

If n represents the number 2, Q preferably represents the 1,3-phenylene, 4,4′-diphenyl ether or 4,4′-diphenylsulphone group, particularly however the 4,4′-diphenylmethane group.

The isoimides of the formula II are known per se [see U.S. Pat. Nos. 2,980,701, 2,995,577, 2,998,429, 3,035,065 and 3,144,435; Journal of Polymer Science: Polymer Chemistry Edition, 13, 1691–1698 (1975)], or they can be produced in a manner known per se by dehydration of the corresponding maleamic acids.

If M represents, where z is 1, an unsubstituted or substituted phenyl or naphthyl group, these groups are, in particular, unsubstituted naphthyl or phenyl groups, or phenyl groups which are substituted by a nitro or hydroxyl group, or by 1 to 3 alkyl groups each having 1–4 carbon atoms, and/or by halogen atoms, especially Cl or Br.

If M represents, where z is 2, a biphenyl radical, this is, in particular, the 4,4′-biphenyl radical.

The following may be mentioned as suitable compounds of the formula III: phenol, α- and β-naphthol, cresols, xylenols, resorcin, 3-chlorophenol, 4-bromophenol, 2-, 3- or 4-nitrophenol, 2,4-dichlorophenol, 2,4,6-tribromophenol and 2,4,6-trichlorophenol, N-hydroxysuccinimide, N-hydroxy-nadicimide, 2,2′-dihydroxy- and 4,4′-dihydroxybiphenyl as well as 2,2-bis-(4-hydroxyphenyl)-propane ("Bisphenol A").

The compound of the formula III preferably used in the process according to the invention is nitrophenol, α-naphthol or 2,2-bis-(4-hydroxyphenyl)-propane, especially however phenol or 4-hydroxysuccinimide.

Alkyl groups $R_1$, $R_2$ and $R_3$ in formula IV each preferably contain 1–8 carbon atoms; in particular, however, each contain 1 or 2 carbon atoms. Suitable tertiary amines of the formulae IV and V which may be mentioned are: trimethylamine, triethylamine, tri-n-propylamine, tri-n-butylamine, tri-n-amylamine, tri-(2-ethyl-n-hexyl)-amine, tri-n-dodecylamine, cyclohexyldimethylamine, phenyldimethylamine, benzyl-diethylamine, tribenzylamine, dimethylisopropylamine, 2-phenylethyldiethylamine, methylethyl-n-propylamine, 1,2-bis-(dimethylamino)-ethane, 1,6-bis-(dimethylamino)-hexane, 1,4-bis-(dimethylamino)-butane and 1,3-bis-(diethylamino)-propane. Preferably used is 1,2-bis-(dimethylamino)-ethane (N,N,N′,N′-tetramethylethylenediamine) or triethylamine.

The compound of the formula III and the tertiary amine of the formula IV or V are advantageously used each in amounts of about 0.2 to about 10 mol %, and preferably each in amounts of about 2 to 7 mol %, relative to the employed isoimide of the formula II.

The reaction according to the invention is advantageously performed in the presence of an organic diluent or solvent which is inert under the reaction conditions. Suitable solvents or diluents are, e.g., optionally chlorinated aromatic hydrocarbons such as benzene, toluene, xylenes and chlorobenzene; chlorinated aliphatic hydrocarbons such as chloroform, methylene chloride and 1,2-dichloroethane; aliphatic and cycloaliphatic ketones such as acetone, methyl ethyl ketone and cyclohexanone; as well as aliphatic and cyclic ethers such as diethyl ether and dioxane. Preferred solvents or diluents are acetone, methylene chloride, benzene and toluene.

The conversion according to the invention is advantageously performed at a reaction temperature of about 10 to 40° C.

The process according to the invention can be performed easily and without expensive apparatus by suspending or dissolving in the diluent or solvent the isoimide to be converted; adding the compound of the formula III and the tertiary amine; and stirring the reaction mixture without heating, or simply allowing it to stand. The reaction in many cases is slightly exothermic. The degree of conversion to the imide can be easily determined, e.g. by means of IR spectrum or thin-layer chromatography.

In the process according to the invention, it is also possible to use mixtures of isoimides and imides, as can be obtained, for example, on reaction of amide acids of the formula VI

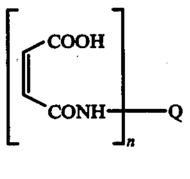

(VI), wherein Q and n have the meanings given under formula I, with ketene.

After completion of the reaction, the imides of the formula I can be isolated in a manner known per se, and optionally purified, e.g. by removal of the solvent or diluent and digestion of the residue in water or methanol to effect removal of the catalysts. Insoluble imides can be obtained by filtration directly in the pure form.

The imides of the formula I are obtained in a very pure form and in good to very good yields by the process according to the invention. Furthermore, interfering secondary reactions can be to a great extent avoided by virtue of the mild reaction conditions.

The imides of the formula I are in most cases known [see, inter alia, DT-AS 1,445,958, DT-OS 2,040,094, U.S. Pat. Nos. 2,444,536, 3,018,290 and 3,018,292]. They are used, for example, as insecticides and fungicides, or they can be used for the production of polymers.

EXAMPLE 1

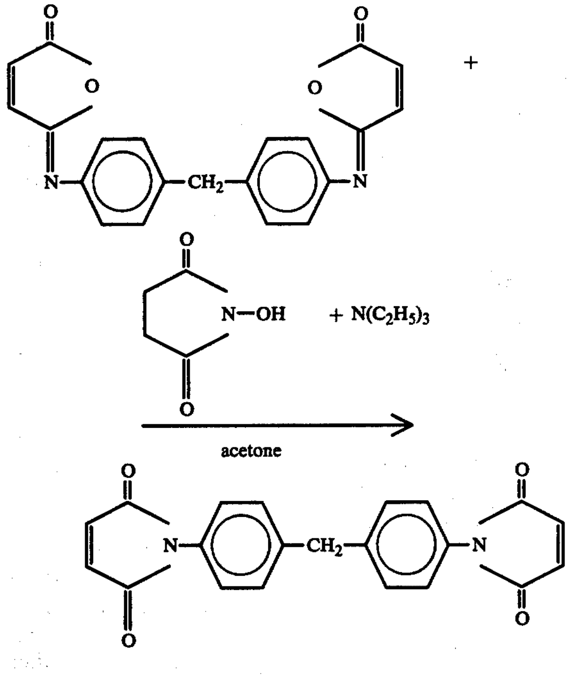

20 g (0.056 mole) of N,N',4,4'-diphenylmethane bis-isomaleimide is suspended in 100 ml of acetone. 0.200 g (0.0017 mole) of N-hydroxysuccinimide and 0.3 ml (0.218 g; 0.0022 mole) of triethylamine are then added. The reaction mixture is stirred for 24 hours at 20°–25° C., with precipitation of the product in crystalline form commencing after about 5 hours. The solvent is removed in a rotary evaporator; the residue is digested in water, filtered off, and dried at 60° C. in vacuo. The yield obtained is 20 g (100% of theory) of N,N',4,4'-diphenylmethane bis-maleimide; m.p. 153–157° C.

IR spectrum ($CHCl_3$): $\lambda_{max.}$, inter alia, 580μ.

Analysis for $C_{21}H_{14}N_2O_4$ (molecular weight = 358.35):

calculated: C 70.39%; H 3.94%; N 7.82%; found: C 70.08%; H 4.04%; $N_{7.86}$%.

EXAMPLE 2

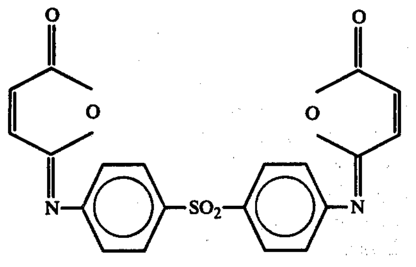

-continued

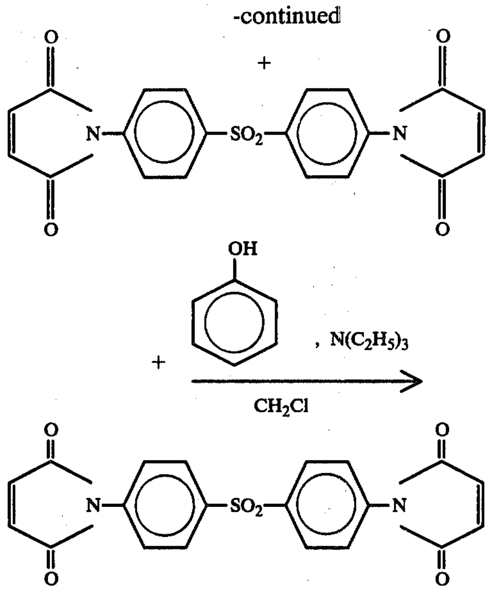

30 g (0.074 mole) of a mixture of N,N',4,4'-diphenylsulphone bis-maleimide and N,N',4,4'-diphenylsulphone bis-isomaleimide are suspended in 100 ml of methylene chloride. To the suspension are added 0.600 g (0.0064 mole) of phenol and 0.6 ml (0.435 g; 0.0043 mole) of triethylamine; the reaction mixture is stirred at 20–25° C. for 4 hours, and the solvent is subsequently removed in the rotary evaporator. The residue is digested with 50 ml of acetone, filtered, and then dried in vacuo at 40° C. The resulting yield is 25.9 g (86% of theory) of light-beige crystalline N,N',4,4'-diphenylsulphone bis-maleimide; m.p about 243° C. (decomposition).

IR spectrum ($CHCl_3$): $\lambda_{max.}$,inter alia, 5.80μ.

Analysis for $C_{20}H_{12}N_2O_6S$ (molecular weight = 408,38):

calculated: C 58.82%; H 2.96%; N 6.86%; S 7.85%; found: C 58.35%; H 2.99%; N 6.76%; S 7.44%.

The mixture of bis-maleimide and bis-isomaleimide used in the above Example is produced as follows:

40.5 g (0.091 mole) of N,N',4,4'-diphenylsulphone bis-maleamic acid is suspended in 400 ml of acetic anhydride. The resulting suspension is heated with a heating bath to 45° C. whilst stirring is maintained; the heating bath is then removed and 0.4 mole of ketene is introduced, whereupon the temperature rises to 48° C. Unreacted amide acid (0.500 g, i.e. 99% conversion) is removed by filtration and the filtrate is rotated. The solid yellow residue is suspended in saturated sodium hydrogen carbonate solution, filtered and subsequently washed with water. Drying in vacuo at 20–25° C. yields 34.8 g (95% of theory) of a product consisting, according to IR spectrum, principally of N,N',4,4'-diphenylsulphone bis-maleimide with smaller porportions of N,N',4,4'-diphenylsulphone bis-isomaleimide; m.p 195–205° C.

EXAMPLE 3

20 g (0.056 mole) of N,N',4,4'-diphenylmethane bis-isomaleimide is suspended in 100 ml of acetone. To the suspension are added 0.400 g (0.0034 mole) of N-hydroxysuccinimide and 0.6 ml (0.0043 mole) of triethylamine, and the reaction mixture is stirred at 20–25° C. for 2½ hours. Several drops of anhydrous acetic acid are subsequently added, and the greater part of the solvent is removed in the rotary evaporator. To the residue is added 50 ml of water; the resulting precipitate is filtered off and washed with water. The residue is dried at 60° C. in vacuo to leave 18.7 g (93% of theory) of N,N',4,4'-diphenylmethane bis-maleimide, m.p. 156–158° C.

IR spectrum ($CHCl_3$): $\lambda_{max.}$, inter alia, 5.80μ.

EXAMPLE 4

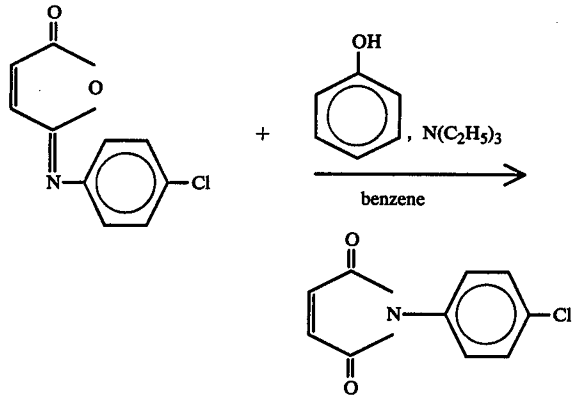

52 g (0.25 mole) of N-p-chlorophenyl isomaleimide is dissolved in 500 ml of benzene. To the solution are added 1.0 g (0.001 mole) of phenol and 1.0 ml (0.073 g; 0.0007 mole) of triethylamine, and the reaction mixture is stirred at 20–25° C. for 6 hours. The reaction mixture is extracted by shaking three times with 200 ml of water each time; the organic phase is dried over calcium chloride, and the benzene is distilled off in a rotary evaporator. To effect removal of the residual phenol, the residue is stirred in 250 ml of water at 60° C. for 90 minutes; it is then filtered off hot, washed with water and dried at 40° C. in vacuo to obtain 42.5 g (81% of theory) of yellow crystalline N-p-chlorophenyl maleimide, m.p. 115–116° C.

IR spectrum ($CHCl_3$): $\lambda_{max.}$, inter alia, 5.80μ.

Analysis for $C_{10}H_6ClNO_2$ (molecular weight = 207.62):

calculated: C 57.85%; H 2.91%; N 6.75%; Cl 17.08%; found: C 57.88%; H 2.71%; N 6.65%; Cl 17.16%.

EXAMPLE 5

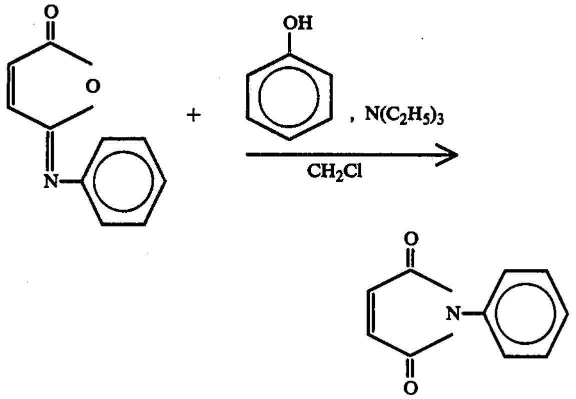

10 g (0.058mole) of N-phenyl isomaleimide is dissolved in 100 ml of methylene chloride. To the solution are added 0.400 g (0.004 mole) of phenol and 0.4 ml (0.290 g; 0.0029 mole) of triethylamine. The reaction mixture is stirred at 20–25° C. for 3 hours, and is then extracted by shaking twice with 10% aqueous NaOH solution; it is washed twice with water, dried over sodium sulphate and the solvent is removed in a rotary evaporator. The residue is dried at 40° C. in vacuo to obtain 9.7 g (97% of theory) of yellow crystalline N-phenyl maleimide, m.p. 85–86° C.

In spectrum ($CHCl_3$): $\lambda_{max.}$, inter alia, 5.80μ.

Analysis for $C_{10}H_7NO_2$ (molecular weight = 173.17): calculated: C 69.36%; H 4.08%; N 8.09%; found: C 69.11%; H 4.15%; N 7.92%.

EXAMPLE 6

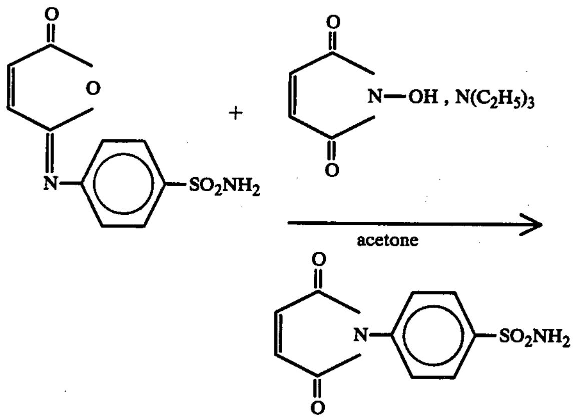

25.9 g (0.103mole) of N-p-sulphamoylphenyl isomaleimide, produced from the corresponding amide acid by reaction with dicyclohexylcarbodiimide in acetone, is dissolved in 300 ml of acetone. There are then added 0.23 g (0.002 mole) of N-hydroxysuccinimide and 0.25 g (0.0025 mole) of triethylamine. The temperature of the reaction mixture rises to 30° C., and after a short time the product commences to precipitate in crystalline form. The reaction mixture is stirred for a further hour; it is then concentrated by evaporation to about half, and allowed to cool for several hours. The product is filtered off, and dried at 20–25° C. in vacuo. From the mother liquor it is possible to obtain, by concentrating by evaporation and crystallising out in a refrigerator, a further 2.6 g of product. Total yield is 22.3 g (86% of theory) of colourless crystalline N-p-sulphamoylphenyl maleimide, m.p. about 200° C., (decomposition).

IR spectrum (Nujol): $\lambda_{max.}$, inter alia, 5.75/5.85μ.

Analysis for $C_{10}H_8N_2O_4S$ (molecular weight = 252.24):

calculated: C 47.62%; H 3.20%; N 11.11%; S 12.71%; found: C 47.58%; H 3.12%; N 11.22%; S 12.60%.

EXAMPLE 7

79.0 g (0.22 mole) of N,N',4,4'-diphenylmethane bis-isomaleimide is dissolved in 400 ml of methylene chloride. To the solution are added 1.80 g (0.019mole) of phenol and 1.8 ml (0.013 mole) of triethylamine, and the reaction mixture is stirred at 20–25° C. for 3 hours. There is subsequently added 0.8 ml (0.013 mole) of anhydrous acetic acid, and the solvent is removed in a rotary evaporator at 40° C. The solid residue is suspended twice in 100 ml of methanol each time and filtered, and the residue is dried at 60° C. in vacuo. There is obtained 75.5 g (95.5% of theory) of N,N',4,4'-diphenylmethane bis-maleimide, m.p. 156–158° C.

IR spectrum ($CHCl_3$): $\lambda_{max.}$, inter alia, 5.80μ.

the solvent is then removed. The yields of N-phenyl maleimide are given in the following Table.

| Ex. No. | Compound of the formula III | N-phenyl malemide obtained g | % of theory | m.p. ° C |
|---|---|---|---|---|
| 12 | 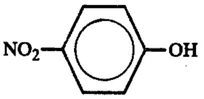 | 2,4 | 92 | 87-88 |
| 13 | 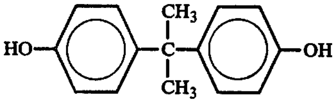 | 2,6 | 100 | 82-84 |
| 14 | 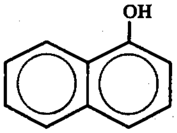 | 2,6 | 100 | 82-84 |

I claim:

1. Process for the production of an imide of the formula I

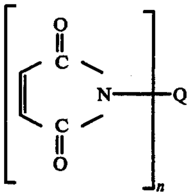 (I)

wherein n represents the number 1 or 2,

Q represents, if n is 1, phenyl, 1-naphthyl, 2-naphtyl, or said phenyl or said naphthyl groups substituted by 1 to 3 moieties selected from the group consisting of halogen, hydroxyl, alkyl of 1 to 8 carbon atoms, halogenoalkyl of 1 to 3 carbon atoms, alkylthio of 1 to 4 carbon atoms, N,N-dialkylamino of 1 to 4 carbon atoms, alkoxy of 1 to 4 carbon atoms, phenoxy, alkoxycarbonyl of 2 to 5 carbon atoms; $-SO_2Y$, —NHCOY,

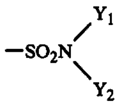 and 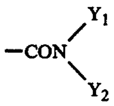

where

Y is phenyl or alkyl of 1 to 4 carbon atoms, $Y_1$ is hydrogen, phenyl, naphthyl or alkyl of 1 to 8 carbon atoms and $Y_2$ is hydrogen or alkyl of 1 to 8 carbon atoms; cyano and nitro; and, if n is 2, Q represents 1,3-phenylene, 1,4-phenylene 1,2-naphthylene, 1,8-naphthylene or 2,3-naphthylene; or said phenylene or naphthylene substituted by 1 to 3 moieties selected from the group given for substituting phenyl or naphthyl for Q when n is 1; or a group of the formulae

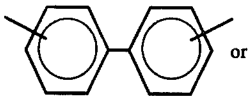 or 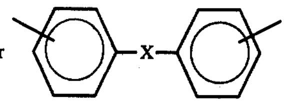

whereby

X represents the bridge member —O—, —S—, —S-S—, $-SO_2-$, $-CH_2-$, —CO— or

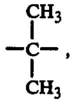, which process comprises converting an isoimide of the formula II

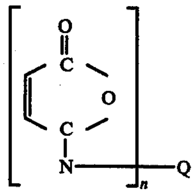 (II), wherein Q and n have the meanings given under the formula I, in the presence of a compound of the formula III $$M-(OH)_z \quad (III)$$

and of a teriary amine of the formula IV or V

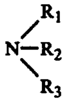 or 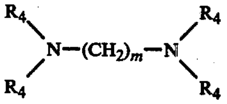

(IV) (V)

wherein z represents the number 1 or 2, m represents an integer from 2 to 6,

M represents, where z is 1, phenyl, naphthyl or said phenyl substituted by 1 to 3 moieties selected from the group consisting of nitro, hydroxyl, alkyl of 1 to 4 carbon atoms and halogen, or a group

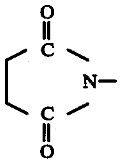 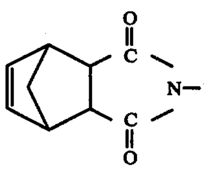 and, where z is 2, a group

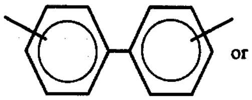 or 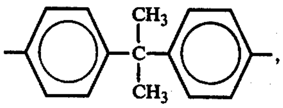, $R_1$ and $R_2$ independently of one another represent an alkyl group having 1 to 16 carbon atoms, a cycloalkyl group having 3 to 12 carbon atoms, or benzyl,

EXAMPLE 8

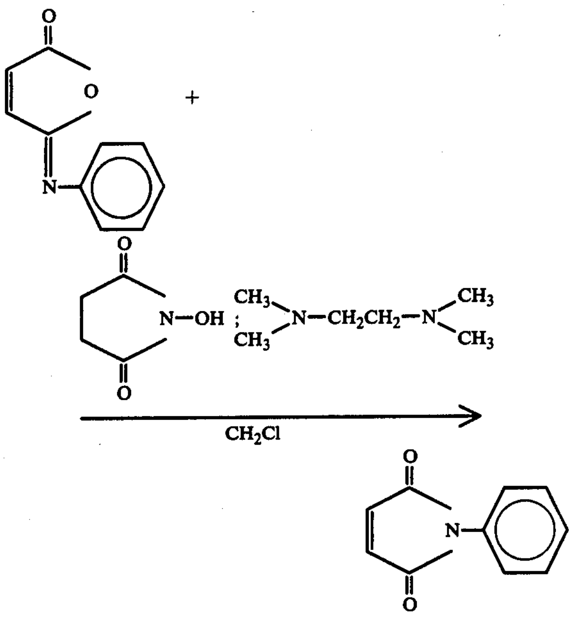

5.2 g (0.03 mole) of N-phenyl isomaleimide is placed into 50 ml of methylene chloride. There are then added 0.103 g (0.0009 mole) of N-hydroxysuccinimide and 0.319 g (0.0012 mole) of N,N,N',N'-tetramethylethylenediamine. After the reaction mixture has been stirred at 20–25° C. for two hours, the IR spectroscopic analysis of the reaction mixture indicates complete isomerisation to the imide. The resulting yellow solution is shaken out twice with water. After removal of the solvent there remain 5.1 g (98% of theory) of yellow crystalline N-phenyl maleimide, m.p. 84–85° C.

IR spectrum ($CHCl_3$): $\lambda_{max.}$, inter alia, 5.80μ.

EXAMPLE 9

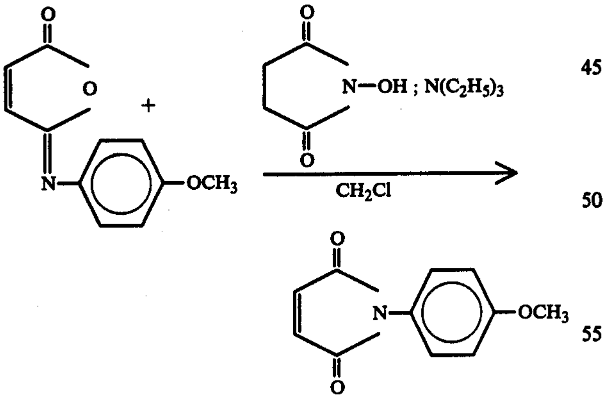

0.276 g (0.0024 mole) of N-hydroxysuccinimide and 0.323 g (0.0032 mole) of triethylamine are added to 16.2 g (0.08 mole) of N-p-methoxyphenyl isomaleimide in 300 ml of methylene chloride. The resulting solution is stirred for 24 hours at 20–25° C., and then extracted by being shaken twice with 300 ml of water each time. The yield after removal of the solvent is 16.3 g (100% of theory) of brownish crystals, m.p. 141–143° C. (crude product; sintering at 137° C.). By recrystallisation of 1 g of these crystals from hot benzene, there is obtained 0.60 g of beige crystals, m.p. 147–149° C. (sintering at 145° C.).

IR spectrum ($CHCl_3$): $\lambda_{max.}$, inter alia, 5.80μ.

Analysis for $C_{11}H_9NO_3$ (molecular weight 203.20): calculated: C 65.02%; H 4.47%; N 6.90%; found: C 65.30%; H 4.69%; N 7.07%.

EXAMPLE 10

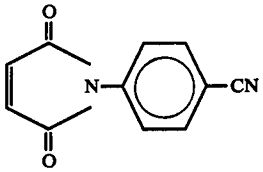

0.276 g (0.0024 mole) of N-hydroxysuccinimide and 0.323 g (0.0032 mole) of triethylamine are added to 15.8 g (0.08 mole) of N-p-cyanophenyl isomaleimide in 300 ml of methylene chloride. The solution obtained is stirred for 2 hours at 20-25° C., and then extracted by being shaken twice with 300 ml of water each time. There is obtained on removal of the solvent 16.0 g (100% of theory) of N-p-cyanophenyl maleimide in the form of yellowish crystals; m.p. 132-134° C.

IR spectrum ($CHCl_3$): $\lambda_{max.}$, inter alia, 4.50 and 5.80μ.

Analysis for $C_{11}H_6N_2O_2$ (molecular weight = 198.18):

calculated: C 66.67%; H 3.05%; N 14.14%; found: C 66.66%; H 3.44%; N 13.86%.

EXAMPLE 11

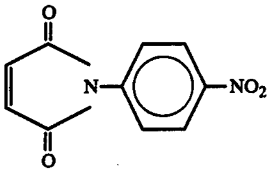

0.276 g (0.0024 mole) of N-hydroxysuccinimide and 0.323 g (0.0032 mole) of triethylamine are added to 17.4 g (0.08 mole) of N-p-nitrophenyl isomaleimide in 300 ml of methylene chloride. The resulting solution is stirred at 20–25° C. for 2 hours and then extracted by being shaken twice with 300 ml of water each time. After removal of the solvent, there remains 17.7 g (100% of theory) of crude N-p-nitrophenyl maleimide. 1 g of this is recrystallised hot from 25 ml of benzene to obtain 0.7 g of pure N-p-nitrophenyl maleimide in the form of yellowish crystals; m.p. 163–165° C.

IR spectrum ($CHCl_3$): $\lambda_{max.}$, inter alia, 5.80μ.

Analysis for $C_{10}H_6N_2O_2$ (molecular weight = 218.17):

calculated: C 55.05%; H 2.77%; N 12.84%; found: C 55.74%; H 3.12%; N 12.68%.

EXAMPLES 12-14

To 2.6 g (0.015 mole) of N-phenyl isomaleimide in 50 ml of methylene chloride are added 0.00045 mole of the compounds of the formula III which are given below and 0.069 g (0.0006 mole) of N,N,N',N'-tetramethylethylenediamine. The reaction mixture is stirred for two hours at 20–25° C. and is subsequently extracted by being shaken twice with 100 ml of water each time and $R_3$ represents an alkyl group having 1 to 16 carbon atoms, phenyl, benzyl or phenylethyl, and $R_4$ represents methyl or ethyl, at a temperature of about 0–80° C., to an imide of the formula I, and wherein the compound of formula III and the tertiary amine of formula IV or V are each used in amount of 0.2 to 10 mol %, relative to the isoimide of formula II.

2. Process according to claim 1, wherein there is used an isoimide of the formula II in which n represents the number 1, and Q represents the 1- or 2-naphthyl group or a phenyl group which is substituted by 1 or 2 halogen atoms, an alkyl or alkoxy group each having 1–4 carbon atoms in the alkyl moieties, a trifluoromethyl, sulphamoyl, nitro or cyano group.

3. Process according to claim 1, wherein there is used an isoimide of the formula II in which n represents the number 1, and Q represents phenyl.

4. Process according to claim 1, wherein there is used an isoimide of the formula II in which n represents the number 2, and Q represents the 1,3-phenylene group, the 4,4'-diphenyl ether group, the 4,4'-diphenylsulphone group or the 4,4'-diphenylmethane group.

5. Process according to claim 1, wherein the employed compound of the formula III is nitrophenol, α-naphthol, 2,2-bis-(4-hydroxyphenyl)-propane and phenol or N-hydroxysuccinimide.

6. Process according to claim 1, wherein the tertiary amine used is 1,2-bis-(dimethylamino)-ethane or triethylamine.

7. Process according to claim 1, wherein the conversion is performed at a temperature of about 10 to 40° C.

8. Process according to claim 2 wherein said phenyl group is substituted by alkyl of 1 to 2 carbon atoms or by alkoxy of 1 to 2 carbon atoms.

9. Process according to claim 4 wherein Q represents the 4,4'-diphenylmethane group.

10. Process according to claim 5 wherein the compound for formula III is phenol or N-hydroxysuccinimide.

11. Process according to claim 1 wherein the compound of formula III and the tertiary amine of formula IV or V are each used in the amounts of about 2 to 7 mol %, relative to the isoimide of formula II.

* * * * *